United States Patent
Hahn et al.

[11] Patent Number: 5,987,681
[45] Date of Patent: Nov. 23, 1999

[54] ELECTRIC TOOTHBRUSH

[75] Inventors: Matthias Hahn, Frankfurt; Klaus Höfer, Hanau; Andreas Rühmkorff, Dietzenbach, all of Germany

[73] Assignee: Rowenta -Werke GmbH, Offenbach a.M., Germany

[21] Appl. No.: 09/001,868

[22] Filed: Dec. 31, 1997

[51] Int. Cl.[6] .......................... A61C 17/00; A46B 13/02
[52] U.S. Cl. .................................................. 15/22.1
[58] Field of Search ............................. 15/22.1, 22.2, 15/22.3, 22.4, 23, 28; 433/122, 123; 601/141, 142

[56] References Cited

U.S. PATENT DOCUMENTS

| | | | |
|---|---|---|---|
| 3,196,299 | 7/1965 | Kott | 15/22.1 |
| 3,358,309 | 12/1967 | Richardson | 15/22.1 |
| 3,685,080 | 8/1972 | Hubner | 15/22.1 |
| 4,295,240 | 10/1981 | Lex | 15/22.1 |
| 4,757,806 | 7/1988 | Muchisky et al. | 15/22.1 |
| 5,421,726 | 6/1995 | Okada | 15/22.1 |
| 5,471,695 | 12/1995 | Aiyar | 15/22.1 |
| 5,590,434 | 1/1997 | Imai | 15/22.1 |
| 5,706,542 | 1/1998 | Okada | 15/22.1 |
| 5,784,743 | 7/1998 | Shek | 15/22.1 |

FOREIGN PATENT DOCUMENTS

| | | | |
|---|---|---|---|
| 75986 | 7/1961 | France | 15/22.1 |
| 2237734 | 5/1991 | United Kingdom | 15/22.1 |

*Primary Examiner*—Gary K. Graham
*Attorney, Agent, or Firm*—Cohen, Pontani, Lieberman & Pavane

[57] ABSTRACT

An electric toothbrush with a handle, a brush head and a shank which connects the handle to the brush head. A rotary motor is arranged in the handle and drives an unbalanced mass. The unbalanced mass driven by the motor is supported on one side or on both sides in the shank close to the brush head and is driven via an extended drive shaft, preferably an intermediate shaft, by the motor.

10 Claims, 1 Drawing Sheet

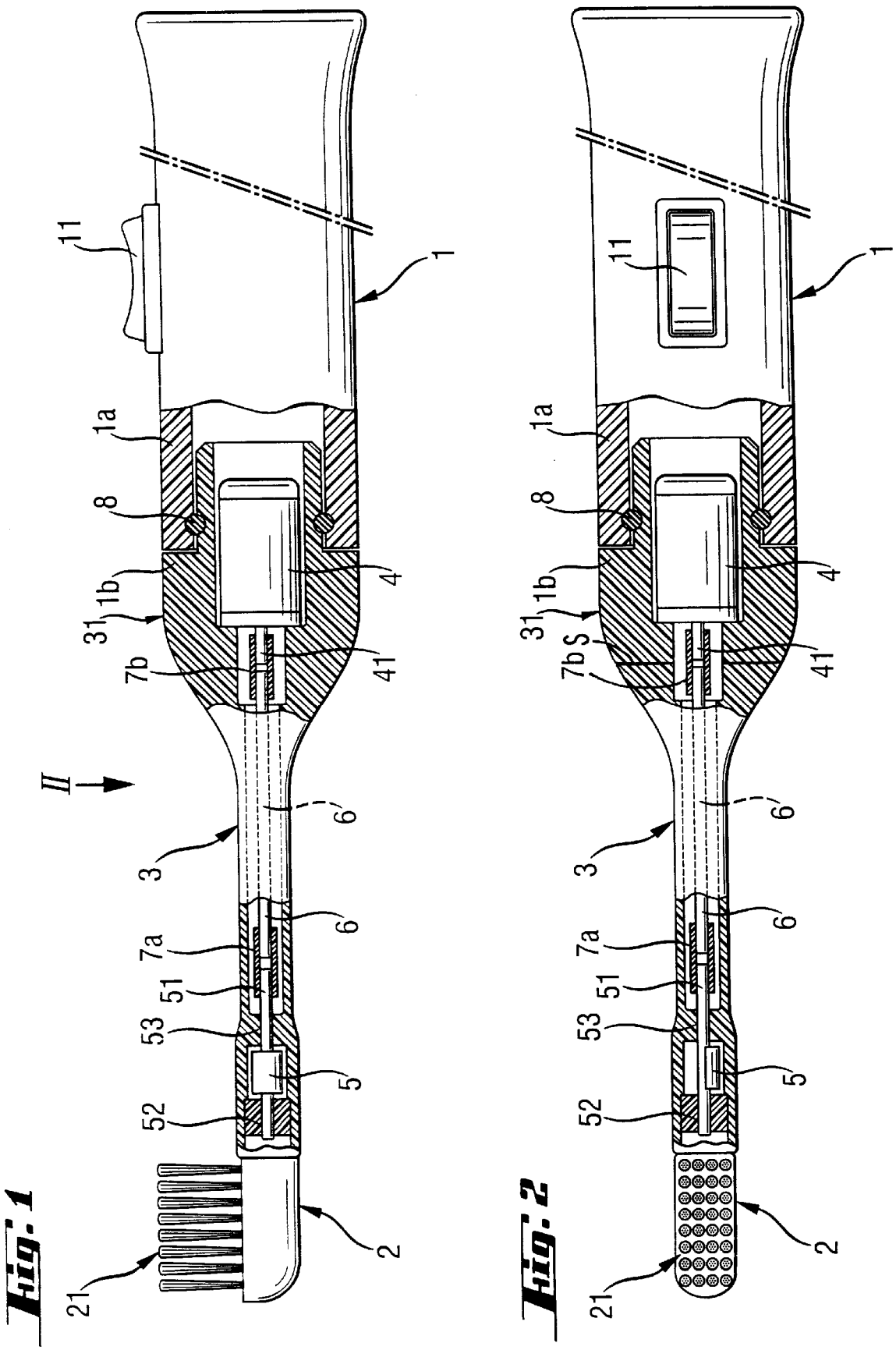

ELECTRIC TOOTHBRUSH

BACKGROUND OF THE INVENTION

1. Field of the Invention

The invention relates to an electric toothbrush.

2. Discussion of the Prior Art

Electric toothbrushes consist of a handle, in which the electric drive is accommodated, a brush head and a shank connecting the brush head to the handle. Electric toothbrushes are known in which the drive consists of a rotary motor, on the shaft butt of which an unbalanced mass is secured in a self-supporting manner. This unbalanced mass is located close to the motor in the handle. The disadvantage of this design consists, on the one hand, in that the handle is strongly influenced by the oscillations (vibrations) generated by the unbalanced mass, which is unpleasant for the user, and, on the other hand, in that the influence of the unbalanced mass on the brush head is relatively feeble. A further disadvantage consists in that the motor is severely loaded by the unbalanced mass that is arranged on its shaft in cantilevered manner, as a result of which its lifespan is shortened.

SUMMARY OF THE INVENTION

The object underlying the invention is to provide an electric toothbrush that is largely freed from the aforementioned disadvantages of an intense vibration of the handle, a poor transmission of the vibrations to the brush head and a severe loading of the motor.

Pursuant to this object, and others which will become apparent hereafter, one aspect of the present invention resides in an electric toothbrush having a handle, a brush head, and a shank that connects the handle to the brush head. A rotary motor is arranged in the handle and drives an unbalanced mass. The unbalanced mass is supported on one side or on both sides in the shank and/or in the brush head, and is driven by an extended drive shaft.

Pursuant to another embodiment of the invention the unbalanced mass is supported in the shank so as to be as close as possible to the brush head.

In still another embodiment the extended drive shaft consists of an intermediate shaft that is coupled on the motor side to a shaft butt of the motor and is coupled on the brush-head side of the shaft to the unbalanced mass.

In yet another embodiment the shaft consists of an integral extension of the motor shaft that is coupled to the shaft of the unbalanced mass.

In yet a further embodiment of the invention the extended drive shaft consists of an integral extension of the shaft or the unbalanced mass that is coupled to the shaft butt of the motor.

In still a further embodiment of the invention the drive shaft is made of a flexible material.

Another embodiment of the invention provides that the couplings on the drive shaft are flexible so that the oscillations originating from the unbalanced mass during operation are damped or decoupled in the direction towards the handle. The couplings can consist of short lengths of tube or hose made of a flexible material that adhere to the ends of the shaft by friction.

In a further embodiment of the invention the shank is constructed on the handle side so that it forms a front most part of the handle in which the motor is accommodated. A damping connection, such as O-ring seals, is provided between the front most handle part and the remaining part of the handle.

In still another embodiment of the invention the shank is provided with a point of separation near to the handle but in front of the motor, as viewed from the brush head. Thus point of separation permits the brush head to be exchanged together with the greater part of the shank. The extended drive shaft is partitioned at this point of separation and is provided with an appropriate coupling.

As a result of the displacement of the unbalanced mass to a position near to or within the brush head, the vibrations generated by the unbalanced mass are transmitted to the brush head to a high degree, whereas they have little effect on the handle.

The invention will be elucidated in more detail on the basis of the embodiment example shown in the Figures. Illustrated are:

BRIEF DESCRIPTION OF THE DRAWINGS

FIG. 1 is a side view of an example of an embodiment of an electric toothbrush according to the invention, partially in section and FIG. 2 is a top view of the toothbrush along to arrow II in FIG. 1, partially in section.

DETAILED DESCRIPTION OF THE PREFERRED EMBODIMENTS

In FIGS. 1 and 2 the handle that takes the form of a casing is designated by 1, the brush head by 2 and the shank connecting the brush head 2 to the handle 1 by 3. The handle 1 is formed substantially by the handle casing 1a. In the embodiment shown, the shank 3 is provided at its end on the handle side with a section 31 that is greatly enlarged in diameter (shank connecting piece) and that forms the front part 1b, located towards the brush head 2, of the handle 1. The motor 4 is accommodated in this enlarged shank connecting piece 31. The electrical lead, which is not represented, to the motor is guided through the handle 1 via the switch 11.

The unbalanced mass 5 is arranged at the end of the shank 3 on the brush-head side, close to the brush head 2. It is provided with its own shaft 51 which is supported on both sides in the bearings 52, 53. The drive shaft is extended as far as the shaft 51 of the unbalanced mass, specifically by means of an intermediate shaft 6 which connects the motor-shaft butt 41 to the shaft 51 of the unbalanced mass. The connections preferably consist of flexible couplings, which in the embodiment that is shown consist of short lengths 7a, 7b of tube or hose that adhere to the ends of the shafts 6, 41, 51 by friction. The brush head 2 bearing the array of bristles 21 is secured to the free end of the shank 3 in a known manner which is not represented, for example by attachment by means of a clip fastener.

In the course of operation of the toothbrush the unbalanced mass 5 rotates, as a result of which the centrifugal force arising leads to intense oscillations which have the stronger effect at the brush head 2, the closer the unbalanced mass is arranged to the brush head. Conversely, these oscillations are largely damped or decoupled in the direction towards the handle 1—to be specific, on the one hand through the use of flexible couplings 7a, 7b and on the other hand by virtue of the fact that the intermediate shaft 6 is constructed from flexible material. A further decoupling of the oscillations from the main part 1a of the handle which is held by the hand of the user is obtained by virtue of the arrangement of the motor in the enlarged shank end 31—to be specific, in particular by means of a damping O-ring seal 8 arranged between the connecting bearing surfaces pertaining to the shank end 31 and the main handle part 1*a*.

In the embodiment example shown, the left-hand bearing of the shaft 51 of the unbalanced mass is constituted by a ring 52 that is inserted into the shank, whereas the bearing 53 is constituted directly by parts of the inner shank wall that are pulled forward in the direction towards the center line of the shank. Of course, the last-mentioned bearing 53 may also consist of an inserted bearing ring.

The embodiment shown in the Figures may be varied in many ways. The intermediate shaft 6 may be dispensed with, either by the motor shaft being extended integrally as far as the coupling 7*a* of the shaft 51 of the unbalanced mass 5 or, conversely, by the shaft 51 of the unbalanced mass being extended integrally as far as the coupling 7*b* on the shaft butt 41. In principle it is also possible for the unbalanced mass 5 to be situated on a motor shaft that is extended integrally as far as the brush head, said motor shaft being additionally supported close to the brush head, but this embodiment is not really suitable from the point of view of manufacture.

Instead of being supported on two sides, as in the illustrated embodiment, the unbalanced mass 5 may be supported on one side only, on one side or the other.

With an appropriate design of the brush head 2 the unbalanced mass 5 may be arranged in the brush head 2 itself. It is also possible for one of the bearings of the unbalanced mass 5 to be located in the brush head 2 and for the other to be located in the shank 3. In these cases, however, each of the interchangeable brush heads has to be provided with an unbalanced mass or a bearing pertaining to an unbalanced mass. In these cases the shaft of the unbalanced mass is moved out of one of the bearings when the brush head is exchanged.

It is self-evident that the end of the shank on the handle side may also be of different construction and may be smaller in diameter, and that the motor may be arranged further to the rear in the actual handle part 1*a*.

Finally it is also conceivable to provide the handle with a point of separation 5 (shown schematically in FIG. 2) near to the handle but to the left of the motor in the sense of the drawing, said point of separation permitting the brush head to be exchanged together with the greater part of the shank. The extended drive shaft is then partitioned at this point and provided with a plug-in coupling similar to the coupling shown at 7*a*, 7*b* in the Figures.

We claim:

1. An electric toothbrush, comprising:

a handle;

a brush head;

a shank that connects the handle to the brush head;

an unbalanced mass supported on at least one side in one of the shank and the brush head;

a rotary motor arranged in the handle to drive the unbalanced mass;

an extended drive shaft connected between the motor and the unbalanced mass; and short lengths of tubular flexible material that frictionally adhere to ends of the extended drive shaft for coupling the extended drive shaft to the motor and the unbalanced mass so that oscillations originating from the unbalanced mass are one of damped and decoupled in a direction towards the handle.

2. An electric toothbrush according to claim 1, wherein the unbalanced mass is arranged in the shank so as to be as close as possible to the brush head.

3. An electric toothbrush according to claim 1, wherein the motor has a shaft butt and the unbalanced mass has a shaft, the extended drive shaft consisting of an intermediate shaft coupled at a first end to the shaft butt of the motor and at a second end to the shaft of the unbalanced mass.

4. An electric toothbrush according to claim 1, wherein the unbalanced mass has a shaft and the motor has a shaft butt, the extended drive shaft being formed as one piece with the shaft butt and being coupled to the shaft of the unbalanced mass.

5. An electric toothbrush according to claim 1, wherein the motor has a shaft butt and the unbalanced mass has a shaft, the extended drive shaft being formed as one piece with the unbalanced mass, and being coupled to the shaft butt of the motor.

6. An electric toothbrush according to claim 1, wherein the extended drive shaft is made of flexible material.

7. An electric toothbrush according to claim 1, wherein the shank is constructed on a side facing the handle so as to form a foremost part of the handle, the motor being accommodated in the foremost part of the handle.

8. An electric toothbrush according to claim 7, and further comprising damping connection means for connecting the foremost part formed by the shank to a remaining part of the handle.

9. An electric toothbrush according to claim 8, wherein the damping connecting means includes an O-ring.

10. An electric toothbrush according to claim 1, wherein the shank is configured to have a point of separation near the handle but in front of the motor, as viewed from the brush head, the point of separation being configured to permit the brush head to be exchanged together with a substantial portion of the shank, the extended drive shaft being partitioned at this point of separation, and a shaft coupling being provided on the extended drive shaft at the point separation.

* * * * *